(12) United States Patent
Nakayama et al.

(10) Patent No.: US 6,774,087 B1
(45) Date of Patent: Aug. 10, 2004

(54) LIQUID HERBICIDE COMPOSITION

(75) Inventors: Kazunari Nakayama, Ciba-ken (JP); Chiako Kamihara, Ciba-ken (JP)

(73) Assignee: FMC Corporation, Philadelphia, PA (US)

(*) Notice: Subject to any disclaimer, the term of this patent is extended or adjusted under 35 U.S.C. 154(b) by 141 days.

(21) Appl. No.: 10/018,939

(22) PCT Filed: Jun. 21, 2000

(86) PCT No.: PCT/US00/17047

§ 371 (c)(1),
(2), (4) Date: May 20, 2002

(87) PCT Pub. No.: WO00/78139

PCT Pub. Date: Dec. 28, 2000

(30) Foreign Application Priority Data

Jun. 22, 1999 (JP) ............................................. 11-175161

(51) Int. Cl.[7] ............................................. A01N 43/653
(52) U.S. Cl. ..................................................... 504/273
(58) Field of Search ........................................... 504/273

(56) References Cited

U.S. PATENT DOCUMENTS 5,935,905 A   8/1999   Mito

FOREIGN PATENT DOCUMENTS

| | | |
|---|---|---|
| DE | 19638887 | 3/1998 |
| EP | 0 648 414 | 4/1995 |
| EP | 1 138 201 | 10/2001 |
| JP | 61289004 | 12/1986 |
| JP | 10045516 | 2/1998 |
| WO | WO 99 51099 | 10/1999 |

*Primary Examiner*—Alton N. Pryor
(74) *Attorney, Agent, or Firm*—FMC Corporation

(57) ABSTRACT

A novel liquid herbicide composition containing carfentrazone-ethyl, an anionic surfactant, a water-soluble organic compound and water and having a pH of from 2 to 7 is provided in which carfentrazone-ethyl is prevented from being in storage.

12 Claims, No Drawings

LIQUID HERBICIDE COMPOSITION

This application is a 371 of PCT/US00/17047 field Jun. 21, 2000.

FIELD OF THE INVENTION

The present invention relates to a liquid composition, which contains carfentrazone-ethyl (common name) and has improved storage stability.

BACKGROUND OF THE INVENTION

Carfentrazone-ethyl is a compound that acts as a herbicide for foliage treatment in upland farming, and exhibits excellent herbicidal activity against all harmful broad-leaved weeds. Carfentrazone-ethyl degrades little and has good storage stability in solid compositions including granules, wettable granules, etc. However, in liquid compositions containing water as a medium it is hydrolyzed by water. Therefore, improving the storage stability of carfentrazone-ethyl in such liquid compositions is much desired.

SUMMARY OF THE INVENTION

Accordingly, the object of the present invention includes a liquid herbicide composition with good storage stability in which carfentrazone-ethyl is prevented from being degraded in storage. More specifically, the present invention is a liquid herbicide composition containing carfentrazone-ethyl, an anionic surfactant, a water-soluble organic compound and water and having a pH of from 2 to 7.

DETAILED DESCRIPTION OF THE INVENTION

A liquid herbicide composition of the following [1] to [10] (hereinafter referred to as "the composition of the inventions") has now been found in which carfentrazone-ethyl is prevented from being degraded in storage.

[1] A liquid herbicide composition containing carfentrazone-ethyl, an anionic surfactant, a water-soluble organic compound and water and having pH of from 2 to 7.

[2] The liquid herbicide composition of [1] above, which has a viscosity of from 1 to 150 mPaS.

[3] The liquid herbicide composition of [2] above, which has a viscosity of from 1 to 100 mPaS.

[4] The liquid herbicide composition of any of [1] to [3] above, which has a pH of from 2 to 6.

[5] The liquid herbicide composition of any of [1] to [4] above, wherein an aqueous 5 wt. % solution of the anionic surfactant has pH of from 1 to 7.

[6] The liquid herbicide composition of any of [1] to [5] above, wherein the anionic surfactant is at least one selected from sulfate-type surfactants and phosphate-type surfactants.

[7] The liquid herbicide composition of [6] above, wherein the sulfate-type surfactant is at least one selected from polyoxyethylene monostyrylphenyl ether sulfates, polyoxyethylene distyrylphenyl ether sulfates and polyoxyethylene tristyrylphenyl ether sulfates, and their salts.

[8] The liquid herbicide composition of [6] above, wherein the phosphate-type surfactant is at least one selected from polyoxyethylene monostyrylphenyl ether phosphates, polyoxyethylene distyrylphenyl ether phosphates and polyoxyethylene tristyrylphenyl ether phosphates, and their salts.

[9] The liquid herbicide composition of any of [1] to [8] above, which is in the form of a suspension.

[10] The liquid herbicide composition of [9] above, which is in the form of a microemulsion.

To produce the composition of the invention, the components are gently mixed and stirred, and the composition thus produced could readily be in the form of a uniform liquid composition. To produce it, therefore, any conventional stirring machines can be used. To that effect, the composition has the advantage of productivity.

The anionic surfactant usable in the invention includes the following (a) to (d).

(a) Carboxylic acid-type surfactants:

For example, they include carboxylic acids such as polyacrylic acids, polymethacrylic acids, polymaleic acids, copolymers of maleic acid and olefins (e.g., isobutylene, diisobutylene, etc.), copolymers of acrylic acid and itaconic acid, copolymers of methacrylic acid and itaconic acid, copolymers of maleic acid and styrene, copolymers of acrylic acid and methacrylic acid, copolymers of acrylic acid and methyl acrylate, copolymers of acrylic acid and vinyl acetate, copolymers of acrylic acid and maleic acid, N-methyl-$(C_{12}-C_{18})$ fatty acid sarcosinates, resin acids, $(C_{12}-C_{18})$ fatty acids, etc.; and salts of such carboxylic acids.

(b) Sulfate-type surfactants:

For example, they include sulfates such as $(C_{12}-C_{18})$ alkyl sulfates, polyoxyethylene $(C_{12}-C_{18})$ alkyl ether sulfates, polyoxyethylene (mono or di)$(C_8-C_{12})$ alkylphenyl ether sulfates, sulfates of polymers of polyoxyethylene (mono or di)$(C_8-C_{12})$ alkyliphenyl ethers, polyoxyethylene (mono, di or tri)phenylphenyl ether sulfates, polyoxyethylene (mono, di or tri)benzylphenyl ether sulfates, polyoxyethylene (mono, di or tri)styrylphenyl ether sulfates, sulfates of polymers of polyoxyethylene (mono, di or tri) styxylphenyl ethers, sulfates of polyoxyethylene-polyoxypropylene block polymers, sulfated oils, sulfated fatty acid esters, sulfated fatty acids, sulfated olefins, etc.; and salts of such sulfates.

(c) Sulfonic acid-type surfactants:

For example, they include sulfonic acids such as $(C_{12}-C_{22})$ paraffinsulfonic acids, $(C_8-C_{12})$ alkylbentenesulfonic acids, formalin condensates with $(C_8-C_{12})$ alkylbenzenesulfonic acids, formalin condensates with cresolsulfonic acids, $(C_{14}-C_{16})$ a-olefmsulfonic acids, $(C_8-C_{12})$ dialkyl sulfosuccinic acids, lignin sulfonic acids, polyoxyethylene (mono or di)$(C_8-C_{12})$ alkylphenyl ether sulfonic acids, half esters of polyoxyethylene $(C_{12}-C_{18})$ alkyl ether sulfosuccinic acids, naphthalenesulfonic acids, (mono or di)$(C_1-C_6)$ alkylnaphthalenesulfonic acids, formalin condensates with naphthalenesulfonic acids, formalin condensates with (mono or di) $(C_1-C_6)$ alkylnaphthalenesulfonic acids, formalin condensates with creosote oil sulfonic acids, $(C_8-C_{12})$ alkyldiphenyl ether disulfonic acids, Igepon T (trade name), polystyrenesulfonic acids, copolymers of styrenesulfonic acid and methacrylic acid, etc.; and salts of such sulfonic acids.

(d) Phosphate-type surfactants:

For example, they include phosphates such as $(C_8-C_{12})$ alkyl phosphates, polyoxyethylene $(C_{12}-C_{18})$ alkyl ether phosphates, polyoxyethylene (mono or di)$(C_8-C_{12})$ alkylphenyl ether phosphates, phosphates of polymers of polyoxyethylene (mono, di or tri)$(C_8-C_{12})$ alkylphenyl ethers, polyoxyethylene (mono, di or tri)phenylphenyl ether phosphates, polyoxyethylene (mono, di or tri)benzylphenyl ether phosphates, polyoxyethylene (mono, di or tri) styrylphenyl ether phosphates, phosphates of polymers of polyoxyethylene (mono, di or tri)styrylphenyl ethers, phosphates of polyoxyethylene-polyoxypropylene block polymers, phosphatidyl cholines, phosphatidyl ethanolimines, polyphosphates (e.g., tripolyphosphate, etc.), etc.; and salts of such phosphates.

Salts of above (a) to (d) include those with alkali metals (lithium, sodium, potassium, etc.), alkaline earth metals (calcium, magnesium, etc.), ammonium and various amines (e.g., alkylamines, cycloalkylamines, aLkanolamines, etc.), etc.

One or more of these surfactants can be used herein either singly or as combined. If desired, the anionic surfactant may be combined with any of nonionic surfactants and cationic surfactants.

Preferably, the anionic surfactant for use in the invention is such that its aqueous 5 wt. % solution has pH of from 1 to 7, more preferably from 1 to 5, in order to further improve the storage stability of carfentrazone-ethyl in the composition.

Also in order to further improve the storage stability of carfentrazone-ethyl in the composition, the anionic surfactant is preferably selected from sulfate-type surfactants and phosphate-type surfactants, including, for example, acids such as polyoxyethylene monostyrylphenyl ether sulfates, polyoxyethylene distyrylphenyl ether sulfates, polyoxyethylene tristyrylphenyl ether sulfates, polyoxyethylene monostyrylphenyl ether phosphates, polyoxyethylene distyrylphenyl ether phosphates, polyoxyethylene tristyrylphenyl ether phosphates, etc., and their salts. Of those, more preferred are polyoxyethylene distyrylphenyl ether sulfates, polyoxyethylene tristyrylphenyl ether sulfates, polyoxyethylene distyrylphenyl ether phosphates and polyoxyethylene tristyrylphenyl ether phosphates, and their salts. Even more preferred are polyoxyethylene tristyrylphenyl ether sulfates and polyoxyethylene tristyrylphenyl ether phosphates, and their salts.

The water-soluble organic compound to be used in the invention is meant to indicate an organic compound having a solubility in water of at least 1% by weight. Concretely, it includes monoalcohols, polyalcohols, glycol ethers, amines, ether amines, etc. Of those, preferred are polyalcohols and glycol ethers. They include, for example, ethylene glycol, propylene glycol, diethylene glycol, hexylene glycol, polyethylene glycol and polypropylene glycol; polyglycols such as glycerin, etc.; glycol ethers such as propyl cellosolve, butyl cellosolve, phenyl cellosolve, propylene glycol monomethyl ether, propylene glycol monoethyl ether, propylene glycol monopropyl ether, propylene glycol monobutyl ether, propylene glycol monophenyl ether, etc. Of these, more preferred are glycols. Even more preferred are ethylene glycol, propylene glycol and diethylene glycol.

The composition of the invention may optionally contain any other agricultural active compounds, for example, phenoxyacetic acid-type compounds, organic phosphorus-containing herbicides, sulfonylurea-type compounds, etc.

The organic phosphorus-containing herbicides include, for example, glyphosate (common name) and its salts (sodium salt, trimesium salt, ammonium salt, etc.), glufosinate (common name) and its salts (sodium salt, trimesium salt, isopropylamine salt, etc.), and bilanafos (common name) and its salts (isopropylamine salt, trimesium salt, ammonium salt, etc.), etc.

The phenoxyacetic acid-type compounds include, for example, 2,4-D (common name), MCPA (common name), MCPB (common name), etc.

The sulfonylurea-type compounds include, for example, pyrazosulfuron ethyl (common name), halosulfuron methyl (common name), benzulfuron methyl (common name), imazosulfron (common name), azimsulfuron (common name), cinosulfuron (common name), cyclosulfamuron (common name), thifensulfuron-methyl (common name), flazasulfuron (common name), metsulfuron-methyl (common name), ethoxysulfuron (common name), etc.

The pH of the composition of the invention falls between 2 and 7. However, in order to further improve the storage stability of carfentrazone-ethyl therein, its pH preferably falls between 2 and 6, more preferably between 2 and 5.

For controlling the pH of the composition of the invention, for example, employable is a method of adding a predetermined amount of any of various inorganic or organic acids, such as hydrochloric acid, sulfuric acid, phosphoric acid, sulfonic acids and carboxylic acids, or their salts or esters, to the liquid herbicide composition. Concretely, the organic acids include acid phosphoric esters, citric acid, maleic acid, sorbic acid, lactic acid, tartaric acid, etc. As the case may be, a predetermined amount of a buffer, such as an aqueous solution of disodium hydrogenphosphate-citric acid, an aqueous solution of sodium acetate-hydrochloric acid, an aqueous solution of formic acid-sodium formate, an aqueous solution of lactic acid-sodium lactate, an aqueous solution of tartaric acid-sodium tartrate, an aqueous solution of sodium citrate-hydrochloric acid or the like, may be added thereto to control the pH of the composition.

The pH of the liquid herbicide composition is measured with a glass electrode-type pH meter, at 25° C. To measure it, used is a thick liquid of the composition.

The viscosity of the composition of the invention is not specifically defmed. In view of the easiness in actually handling the composition, its viscosity preferably falls between 1 and 150 mPas, more preferably between 1 and 100 mPas, most preferably between 1 and 50 mPas.

The viscosity of the liquid herbicide composition is measured with a Brooldield viscometer (Model DV-III from Brookfield) equipped with a No. 3 rotor, at 30 rpm and at 25° C. To measure it, used is a thick liquid of the composition.

Regarding the blend ratio of the constituent components of the composition of the invention, it is desirable that the composition contains from 0.01 to 10 parts by weight, preferably from 0.1 to 2.0 parts by weight, relative to 100 parts by weight of the composition, of carfentrazone-ethyl; from 1.0 to 60.0 parts by weight, preferably from 5.0 to 40.0 parts by weight of other agricultural active compounds; from 1 to 20 parts by weight, preferably from 5 to 10 parts by weight of an anionic surfactant; and from 1 to 10 parts by weight of a water-soluble organic compound.

The form of the composition of the invention is not specifically defined, so far as it is liquid. Preferably, however, the composition is in the form of a suspension. The suspension referred to herein is meant to include a flowable preparation (SC, suspension concentrate), an emulsion in water (EW), a suspoemulsion (SE), a microemulsion (ME), and a multiple emulsion, as so described in Guide to Agricultural Compositions (edited by the members in the Section for the Study of Agricultural Compositions and Their Applications of the Japan Agricultural Chemical Society, published by the Japan Plant Epidemics Prevention Association, 1997). Of those, more preferred is a microemulsion.

Various adjuvants may be in the composition of the invention, including, for example, thickeners, defoaming agents, preservatives, colorants, etc.

The invention is described concretely with reference to the following Examples and Test Example, which, however, are not intended to restrict the scope of the invention.

In the following, parts are all by weight. Carfentrazone-ethyl is referred to as Compound A; N-(phosphonomethyl)

glycine isopropylammonium salt is as Compound B; and N-(phosphonomethyl)glycine trimethylsulfonium salt is as Compound C.

EXAMPLE 1

1.0 part of Compound A was dissolved in 2.0 parts of phenyixylethane. To the resulting solution, were added 2.0 parts of POE alkyl ether (Pegnol TH-8 from Toho Chemical), 5.0 parts of POE tristyrylphenyl ether phosphate (Soprophr 3D33 from Rhone-Poulenc, its aqueous 5 wt. % solution has pH of from 1.5 to 3), 20.0 parts of ethylene glycol and 70.0 parts of distilled water, and stirred to prepare a clear microemulsion. Its pH was 3.1, and its viscosity was 27 mPas.

EXAMPLE 2

1.0 part of Compound A was dissolved in 2.0 parts of phenylxylethane. To the resulting solution, were added 20.0 parts of Compound B, 20.0 parts of quaternary ammonium salt (NK-3000S from Takemoto Yushi), 5.0 parts of POE tristyrylphenyl ether phosphate (Soprophr 4D384 from Rhone-Poulenc, its aqueous 5 wt. % solution has pH of from 2 to 4), 20.0 parts of ethylene glycol and 32.0 parts of distilled water, and stirred to prepare a clear microemulsion. Its pH was 4.9, and its viscosity was 18 mpas.

EXAMPLE 3

1.0 part of Compound A was dissolved in 2.0 parts of phenylxylethane. To the resulting solution, were added 10.0 parts of Compound C, 6.0 parts of alkyl-beef tallow amine (Naimeen T-2 from Nippon Yushi), 5.0 parts of POE tristyrylphenyl ether phosphate (Soprophr 4D384 from Rhone-Poulenc, its aqueous 5 wt. % solution has pH of from 2 to 4), 20.0 parts of ethylene glycol and 32.0 parts of distilled water, and stirred to prepare a clear microemulsion. Its pH was 4.5, and its viscosity was 28 mPas.

EXAMPLE 4

1.0 part of Compound A was dissolved in 2.0 parts of phenyixylethane, which was then absorbed by 3.0 parts of white carbon (Carplex #80D from Shionogi Seiyaku). This was milled in an air mill. To this were added 10.0 parts of Compound C, 6.0 parts of alkyl-beef tallow amine (Naimeen T-2 from Nippon Yushi), 5.0 parts of POE tristyrylphenyl ether phosphate (Soprophr 4D384 from Rhone-Poulenc, its aqueous 5 wt. % solution has pH of from 2 to 4), 20.0 parts of ethylene glycol, 10 parts of aqueous 1% solution of xanthane rubber, and 43.0 parts of distilled water, and stirred to prepare an emulsion. Its pH was 4.9, and its viscosity was 96 mPas.

EXAMPLE 5

0.3 parts of Compound A was dissolved in 2.0 parts of phenyixylethane. To the resulting solution, were added 10.0 parts of POE tristyrylphenyl ether phosphate (Soprophr 4D384 from Rhone-Poulenc, its aqueous 5 wt. % solution has pH of from 2 to 4), 20.0 parts of propylene glycol and 67.7 parts of distilled water, and stirred to prepare a clear microemulsion. Its pH was 2.8, and its viscosity was 15 mpas.

Comparative Example 1

1.0 part of Compound A was dissolved in 2.0 parts of phenyixylethane. To the resulting solution, were added 20.0 parts of Compound B, 20.0 parts of quaternary ammonium salt (NK-3000S from Takemoto Yushi), 10.0 parts of POE alkyl ether (Pegnol TH-8 from Toho Chemical), 20.0 parts of ethylene glycol and 27.0 parts of distilled water, and stirred to prepare a clear microemulsion. Its pH was 4.9, and its viscosity was 28 mPas.

Comparative Example 2

1.0 part of Compound A was dissolved in 2.0 parts of phenyixylethane. To the resulting solution, were added 20.0 parts of Compound B, 30.0 parts of POE tristyrylphenyl ether (Sorpol T-20 from Toho Chemical), 10.0 parts of ethylene glycol and 37.0 parts of distilled water, and stirred. However, this separated into two layers, and could not form a uniform liquid composition.

Comparative Example 3

1.0 part of Compound A was dissolved in 2.0 parts of phenylxylethane. To the resulting solution, were added 20.0 parts of Compound B, 30.0 parts of quaternary ammonium salt (NK-3000S from Takemoto Yushi), 10.0 parts of ethylene glycol and 37.0 parts of distilled water, and stirred. However, this separated into two layers, and could not form a uniform liquid composition.

Test Example

The compositions prepared in the above-mentioned Examples and Comparative Examples were separately put into different laboratory glass bottles all equipped with a stopper, and stored in a thermostat at 50° C. for 10 days. After having been thus stored, they were analyzed for the active compound through reversed-phase high-performance liquid chromatography. The data obtained are given in Table 1. The degradation rate of the active compound in each sample was calculated according to the following formula:

Degradation Rate (%)=(1−a/b)×100

In the formula, "a" indicates the active compound content (%) of the stored sample; and "b" indicates the active compound content (%) of the fresh sample.

TABLE 1

| No. | Anionic Surfactant | Degradation Rate of Compound A | Degradation Rate of Compound B or C |
|---|---|---|---|
| Example 1 | contained | 10.1% | — |
| Example 2 | contained | 6.7% | 1.2% |
| Example 3 | contained | 5.9% | 2.2% |
| Example 4 | contained | 11.2% | 1.2% |
| Example 5 | contained | 12.1% | — |
| Comp. Example 1 | not contained | 48.3% | 1.5% |

As in Table 1, the degradation rate of Compound A in the compositions of Examples 1 to 5 all containing an anionic surfactant was smaller than that in the composition of Comparative Example 1 not containing an anionic surfactant.

In the composition of the present invention, carfentrazone-ethyl is prevented from being degraded in storage, and the composition has good storage stability. To produce the composition, the components are gently mixed and stirred, and the composition thus produced could be readily in the form of a uniform liquid composition. To produce it, therefore, any conventional stirring machines can be used. To that effect, the composition has the advantage of productivity.

While the invention has been described in detail with reference to specific embodiments, it will be apparent to one of ordinary skill in the art that various changes and modifications can be made therein without departing from the spirit and scope thereof.

What is claimed is:

1. A liquid herbicide composition containing carfentrazone-ethyl, an anionic surfactant, a water-soluble organic compound and water and having a pH of from 2 to 7.

2. The liquid herbicide composition as claimed in claim 1, which has a viscosity of from 1 to 150 mPaS.

3. The liquid herbicide composition as claimed in claim 2, which has a viscosity of from 1 to 100 mPaS.

4. The liquid herbicide composition as claimed in any one of claims 1 to 3, which has a pH of from 2 to 6.

5. The liquid herbicide composition as claimed in any one of claims 1 to 3, wherein an aqueous 5 wt. % solution of the anionic surfactant has a pH of from 1 to:7.

6. The liquid herbicide composition as claimed in any one of claims 1 to 3, wherein the anionic surfactant is at least one selected from sulfate surfactants and phosphate surfactants.

7. The liquid herbicide composition as claimed in claim 6, wherein the sulfate surfactant is at least one selected from polyoxyethylene monostyrylphenyl ether sulfates, polyoxyethylene distyrylphenyl ether sulfates and polyoxyethylene tristyrylphenyl ether sulfates, and their salts.

8. The liquid herbicide composition as claimed in claim 6, wherein As the phosphate surfactant is at least one selected from polyoxyethylene monostyrylphenyl ether phosphates, polyoxyethylene distyrylphenyl ether phosphates and polyoxyethylene tristyrylphenyl ether phosphates, and their salts.

9. The liquid herbicide composition as claimed in any one of claims 1 to 3, which is in the form of a suspension.

10. The liquid herbicide composition as claimed in claim 9, which is in the form of a microemulsion.

11. The liquid herbicide composition as claimed in claim 1 in which the amount of anionic surfactant is equal to from 1 to 20 parts by weight relative to 100 parts by weight of the composition.

12. The liquid herbicide composition as claimed is claim 1 in which the amount of anionic surfactant is equal to from 5 to 10 parts by weight relative to 100 parts by weight of the composition.

* * * * *